United States Patent [19]

Walker et al.

[11] 4,450,078
[45] May 22, 1984

[54] MICROFILTRATION DEVICE FOR THE FILTRATION OF COAGULA AND MICROAGGREGATES FROM BLOOD

[75] Inventors: Wolfram H. Walker, Rödermark; Karl H. Gänshirt, Dreieich; Hans Schleussner, Frankfurt, all of Fed. Rep. of Germany

[73] Assignee: Biotest-Serum-Institut GmbH, Frankfurt-Niederrad, Fed. Rep. of Germany

[21] Appl. No.: 427,234

[22] Filed: Sep. 29, 1982

[30] Foreign Application Priority Data

Nov. 14, 1981 [DE] Fed. Rep. of Germany ..... 31453201

[51] Int. Cl.$^3$ ...................... B01D 25/04; B01D 39/16
[52] U.S. Cl. .................................... 210/315; 210/338; 210/342; 210/448; 210/489; 210/927
[58] Field of Search ............... 210/337, 338, 451, 488, 210/489, 927, 315, 342, 446, 448

[56] References Cited

U.S. PATENT DOCUMENTS 4,087,363 5/1978 Rosemeyer et al. ............ 210/489 X
4,243,535 1/1981 Behrends et al. ............... 210/338 X

*Primary Examiner*—Thomas G. Wyse
*Attorney, Agent, or Firm*—Sprung, Horn, Kramer & Woods

[57] ABSTRACT

A microfiltration device for the filtration of coagula and microaggregates from blood and blood components. The device contains a filter chamber with attaching nozzle, a filter cone containing truncoconical filter elements arranged in cascade with diminishing pore size and diminishing surface area, a drip chamber and a tailpiece. The filter chamber and filter cones have different tapers and are at a specific distance apart, the taper of the filter cone from inlet to outlet being greater than the taper of the filter chamber. The filter cone has up to four filter elements, and a spacer which extends into the filter element of smallest pore size and surface area and supports same. Each of the filter elements has at least two opposed ribs running from the base to the apex of the truncated cone. The spacer is constructed such that it serves simultaneously for the support of the ribs and for the support of the filter fabric of the smallest filter element. The device has a capacity of less than 100 ml. It is intended for use in transfusions of preserved blood or blood components, especially massive transfusions.

4 Claims, 9 Drawing Figures

MICROFILTRATION DEVICE FOR THE FILTRATION OF COAGULA AND MICROAGGREGATES FROM BLOOD

BACKGROUND OF THE INVENTION

The invention relates to a microfiltration device for the filtration of coagula and microaggregates from blood.

When blood is stored, microcoagula of an order of magnitude extending from less than 10 μm to over 300 μm form depending on such parameters as blood quality, blood stabilizer solution and method of storage.

The coagula consist mainly of thrombocytes, fibrinogen and other cellular and plasmatic components of the blood.

In the transfusion of preserved blood and blood components there is the danger that these coagula will be carried into the circulatory system, especially in the case of massive transfusions, and lodge primarily in the lung as the "physiological" filter. These coagula can then contribute to the effect of the so-called "wet lung syndrome" or to "transfusion lungs", i.e., to a blockage of the capillary vessels of the lungs. It is for this reason that so-called "transfusion filters" have been included in transfusion kits. These filters are simply screen or mesh filters with average pore sizes of 170 to 310 μm. Thus, DIN 58,360 describes such a transfusion kit and at the same time calls for a surface area of 10 cm² and a mesh opening of at least 310 μm.

In recent years, special filters have been developed, so-called microaggregate or microcoagulum filters, which are capable of filtering coagula from the blood down to the 10 micrometer range. In these microcoagulum filters a distinction is made between sieve filters and depth filters. In depth filters, the filtration effect is based on a non-selective absorption of coagula by a layer of more or less densely packed fibers or by porous foam. Sieve filtration devices, on the other hand, operate with filters of a particular mesh size. There are also combinations of these filtration principles.

A number of requirements are generally established by the clinician for microcoagulum filters. These include a high filtration effectiveness of the unit, a high filtering capacity, a high flow rate, small priming volume, and easy handling of the unit.

Furthermore, such a filter must not produce any undesirable influence on the blood parameters, such as hemolysis etc., even at pressures as high as 400 mm of mercury, or in the administration of several units of preserved blood. Also, it must withstand manipulation, i.e., pressure transfusion, and plugging into other blood packages, without damage to filter and casing. On the other hand, it must be possible to produce it economically as a single-use unit.

In German Gebrauchsmuster No. 7,605,700, a microcoagulum filter is described in which the unit consists of a casing into which up to 5 filters, preferably at least 4 filters, in the form of sieves, are placed. These are in a cascade arrangement, i.e., the blood flows through the sieves one after the other, the next-following sieve having a higher filtering performance than the one before. In this manner a good filtration effect can be accomlished by using a relatively small filter surface area and by loading the filter surfaces selectively.

The device described in the above Gebrauchsmuster also has a drip chamber which is hermetically joined directly to the filtration chamber. The overall device is a sterilizable single-use unit. The sieves have a diminishing filter surface area combined with diminishing pore size, they are preferably constructed in truncoconical form, and they consist preferably of plain sieve filters whose smallest mesh size amount to 10 micrometers. The capacity of the unit amounts to at least 150 ml. Such a device is capable, for example, of filtering approximately five to ten ACD whole blood units stored for about two weeks, within 30 minutes under gravity conditions.

In spite of these relatively desirable properties, this device has often proven to be too large, both with regard to its manipulation and with regard to its capacity. To avoid unnecessary blood loss, the capacity of such a device should be as small as possible. Consequently, smaller devices are have been created. In German Gebrauchsmuster No. 7,923,865 there are described several modifications of the abovementioned device, in which only 2 to 3 filter elements of different characteristics are arranged in series, and which has a capacity of less than 150 ml. The performance of this device, however, has proven to be substantially poorer and its use is limited to the transfusion of single blood packages and erythrocyte concentrates without buffy coat (b.c.).

It is the object of the invention to provide a device which meets microcoagulum filter requirements, i.e., with which, for example, massive transfusions can be performed or preserved whole blood or b.c. erythrocyte concentrates can be filtered, but which has a small capacity combined with sufficient effectiveness and filtering ability.

BRIEF SUMMARY OF THE INVENTION

This object is surprisingly achieved in accordance with the invention by means of a microfiltration device for the filtration of coagula and microaggregates from blood and blood components, containing a filter chamber provided with a coupling nozzle, filter cones having truncoconical filter elements disposed in cascade with diminishing pore size and diminishing surface area, drip chamber and tailpiece, the casing, consisting of the attaching nozzle, filter chamber and drip chamber, being closed in a gas-tight and germ-tight manner, characterized in that the filter chamber and the filter cones have different tapers, the taper of the filter cone from inlet to outlet being greater than that of the filter chamber, and the distance between filter cones and filter chamber amounting to no more than 3 mm; that the filter cone has up to four filter elements and a spacer extending into the filter element of smallest pore width and smallest surface area and supporting the latter, and each of the filter elements is provided with at least two ribs substantially opposite one another and extending from the base to the apex of the truncated cone and projecting no more than 3 mm into the interior of the truncated cone, and the spacer being so constructed that it serves simultaneously as a support for the ribs and as a support of the fabric of the filter element, and that the device has a capacity of less than 100 ml.

Certain constructional measures make it possible with the device of the invention, despite its small capacity of less than 100 ml, preferably 75 ml, to achieve the same filtration performance as that of a microfiltration device of the same filtering principle but having a capacity of more than 150 ml.

For example, with the device of the invention, approximately four to seven ACD whole blood packages stored for approximately two weeks were filtered under gravity conditions within approximately 15 minutes, with the same effectiveness as a device of a capacity of more than 150 ml.

The difference in the taper of the filter chamber from that of the filter cone results in a uniform loading of the outermost filter element and prevents clogging of the device at the level of the inlet.

The distance of no more than 3 mm between the filter chamber and the filter cone is important so that relatively large aggregates or clumps of aggregates that can pass through the nozzle will be unable to clog the device at the inlet or along the length of the filter element.

The ribs running lengthwise over the truncoconical filter elements serve simultaneously as supports for each individual filter element and for spacing the filter elements from one another, and bring about a stabilization of the filter fabric. Without this rib system, the filter fabrics would lie against one another after loading, and this would almost completely destroy the effectiveness of these sieves.

The number of ribs is to be such that good stability of the filter elements is achieved without excessively reducing the filtration surface area.

In a preferred embodiment, which optimally satisfies these requirements, the smallest filter element, i.e., the one with the smallest pore size and filter surface area, is equipped with two ribs and the other, preferably three, filter elements are each equipped with six ribs. The ribs of the smallest filter element are preferably situated opposite one another and coincide with two opposite ribs of the six ribs of the next larger filter element. The six ribs of each of the other filter elements are also coincident with one another. The maximum depth of the ribs, of 3 mm, is important because with the given arrangement the filter sieves cannot contact or rest against one another even in the case of massive transfusions and pressure transfusions, thereby destroying the effectiveness of the filter. The minimum depth may be 1 mm or even less.

The two ribs of the last and smallest filter element are fixed in place by a spacer which extends into the filter cone. This spacer serves simultaneously for the reduction of the capacity and prevents the collapse of the ribs and sieve fabric. It is of such a shape, however, that it virtually does not impair the free filter surface of the smallest filter.

For the overall combination, synthetic materials compatible with blood are used, such as polyamides, polyolefins or polyesters. In a preferred embodiment, the sieve combination and the spacers are made of polyamide, while the filter chamber is made of a polyester, such as polyethylene terephthalate.

The filter elements are preferably sieve filters disposed advantageously upright. A preferred filter combination comprises four filter elements having sieve filters of an average mesh opening of 200, 50, 20 and 10 micrometers, respectively. A desirable combination of sieve surface areas is, for example, 69, 59, 46 and 33 cm$^2$, respectively.

The hermetic sealing or joining together of the filter chamber, filter cone and drip chamber can be achieved by welding, cementing or encasement by injection molding.

An embodiment of the invention is represented in the drawings, and will be explained hereinbelow.

Figure 1:
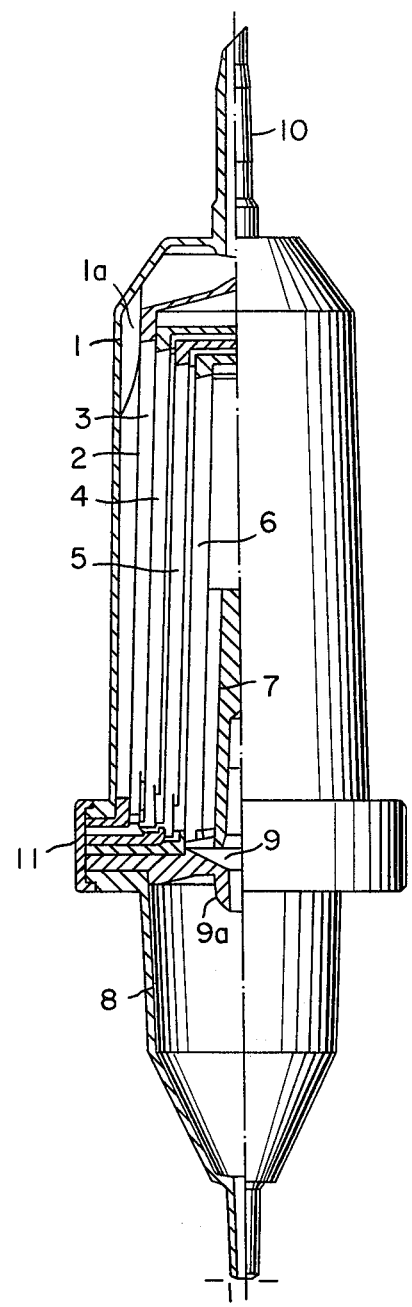
FIG. 1 is an elevational view of the a preferred embodiment of the complete microfiltration device, in which the left half is a vertical cross section through its center.

Referring now more particularly to the drawings, in FIG. 1 there is shown a microfiltration device in accordance with the invention. It consists of a filter chamber 1 with attaching nozzle 10 and inwardly projecting fins 1a for holding the filter cone in place, filter cone 2 with filter elements 3, 4, 5 and 6, which are of truncoconical shape and are arranged in cascade in an upright position, and the spacer 7. As can be seen in this figure, the angle of inclination of the filter cone is greater than the angle of inclination of the filter chamber. Under the base of the last filter element 6, there is an outlet 9 in the form of a plate having a central drain opening 9a in the form of a spout adjoining the drip chamber 8. The filter chamber 1, the filter cone 2, the outlet 9 and the drip chamber 8 are hermetically sealed by a casing 11.

Figure 2:
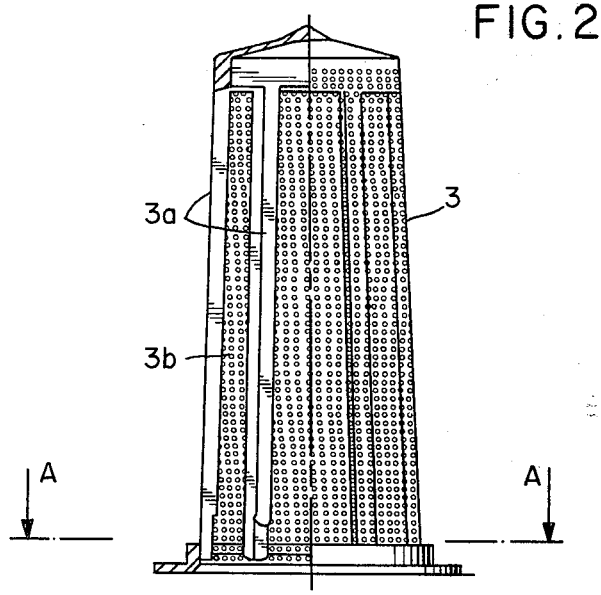
FIG. 2 is an elevational view of a filter element of FIG. 1, a portion being shown in section.

FIG. 2 is an elevational view in which the left half is a vertical cross section through the center of a filter element 3, showing the ribs 3a and the sieve material 3b.

Figure 3:
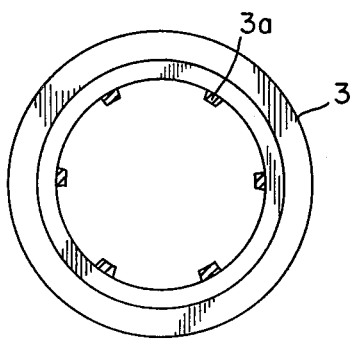
FIG. 3 is a cross section taken along line A—A of FIG. 2.

FIG. 3 is a cross section taken along line A—A of FIG. 2, showing the filter element 3 and six ribs 3a.

Figure 4:
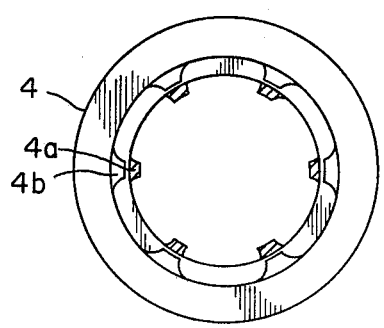
FIG. 4 is a cross section taken at the same elevation as line A—A of FIG. 2 but through the element next adjacent the element of FIG. 2.

FIG. 4 is a cross section through a filter element 4, which corresponds to the cross section A—A of the filter element 3, having six ribs 4a and six recesses 4b for the ribs 3a of filter element 3. A cross section through a filter element 5 would be the same as FIG. 4 except that the inside diameter of the sieve body would be correspondingly smaller.

Figure 5:
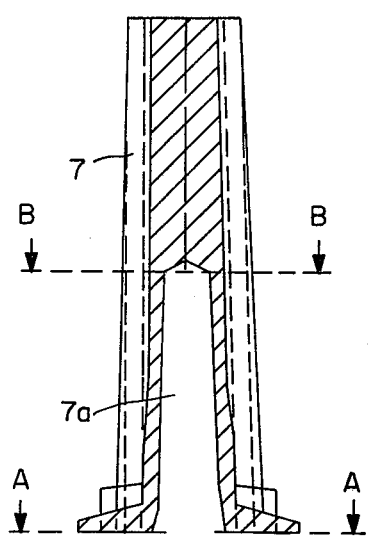
FIG. 5 is a longitudinal cross section through the spacer shown in FIG. 1.

FIG. 5 is a longitudinal cross section through a spacer 7 having a recess 7a.

Figure 6:
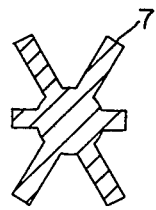
FIG. 6 is a cross section taken along line B—B of FIG. 5.
Figure 7:
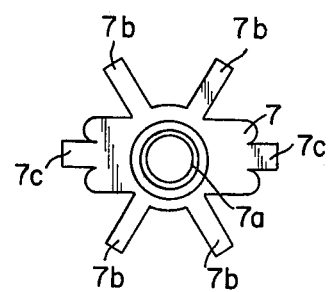
FIG. 7 is a bottom plan view of the spacer of FIG. 5.

FIG. 6 shows a cross section taken through the spacer 7 along line B—B of FIG. 5, while FIG. 7 shows a cross section along line A—A of FIG. 5 of the spacer 7 with the recess 7a as seen from the bottom.

As can be seen in the drawing, the ribs 7b serve for the support of the filter fabric of filter element 6. The two ribs 7c serve to support the two ribs 6a of the smallest filter element 6. The height of the spacer 7 is preferably such that it amounts to half of the height of the filter element 6.

Figure 8:
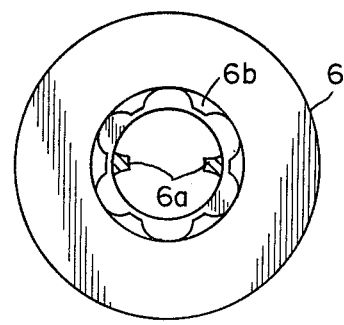
FIG. 8 is a transverse cross section through the innermost filter element.

FIG. 8 shows a cross section through a filter element 6, in which the two ribs 6a and six recesses 6b can be seen, into which the six ribs of the filter element 5 can be snapped.

Figure 9:
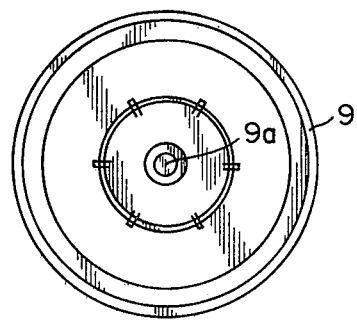
FIG. 9 is a top plan view of the drain element of FIG. 1.

FIG. 9 is a top plan view of the drain 9 with the drain opening 9a.

It is understood that the specification and examples are illustrative but not limitative of the present invention and that other embodiments within the spirit and scope of the invention will suggest themselves to those skilled in the art.

We claim:

1. In a microfiltration device for the filtration of coagula and microaggregates from blood and blood components, comprising a hermetically sealable casing having an attaching nozzle and an outlet, a filter cone with a series of truncoconical filter elements within said casing, the elements from the outermost inwardly having filtering surfaces of successively diminishing pore size and surface area, and a piece provided with an opening separating the inside of the casing into a filter chamber in which the filter cone is located and a drip chamber, the improvement wherein the filter chamber and filter cone have different angles of inclination, the inclination of the filter cone from the inlet to the outlet being greater than the inclination of the filter chamber, and the distance between filter cone and filter chamber amounting to no more than about 3 mm, the filter cone has from two to four filter elements and has a spacer extending into the filter element with the smallest pore size and the smallest surface area and supporting same, and each of the filter elements is equipped with at least two substantially opposite ribs running from the base to the apex of the truncated cone, which extend no more than 3 mm into the interior of the truncated cone, and the spacer is so constructed that it serves simultaneously as support for the ribs and as support of the filter surface of the filter element, the device having a capacity of less than about 100 ml.

2. A microfiltration device according to claim 1, wherein the filter element with the smallest pore size and the smallest surface area is equipped with two ribs and the rest of the filter elements are equipped each with six ribs, the two ribs of the smallest filter element nesting with two opposite ribs of the next filter element, and the six ribs of each of the rest of the filter elements nesting with one another.

3. A microfiltration device according to claim 1, wherein the casing is formed of polyester.

4. A microfiltration device according to claim 1, wherein the filter elements are four uprightly disposed sieve filters with pore sizes of about 200, 50, 20 and 10 micrometers.

* * * * *

UNITED STATES PATENT AND TRADEMARK OFFICE
CERTIFICATE OF CORRECTION

PATENT NO. : 4,450,078

DATED : May 22, 1984

INVENTOR(S) : Wolfram H. Walker et al

It is certified that error appears in the above-identified patent and that said Letters Patent is hereby corrected as shown below:

Under "Foreign Application Priority Data"  Delete "31453201" and substitute --3145320--.

Col. 1, line 39  Before "porous" insert --a--

Signed and Sealed this

Ninth Day of April 1985

[SEAL]

Attest:

DONALD J. QUIGG

Attesting Officer  Acting Commissioner of Patents and Trademarks